United States Patent [19]
Craig

[11] Patent Number: 6,153,147
[45] Date of Patent: Nov. 28, 2000

[54] BEVERAGE ANALYSIS SAMPLE

[76] Inventor: James J. Craig, 785 NE. Harbour Dr., Boca Raton, Fla. 33431

[21] Appl. No.: 09/166,992

[22] Filed: Oct. 6, 1998

[51] Int. Cl.⁷ .................................................. G01N 31/22
[52] U.S. Cl. ................................ 422/59; 422/58; 422/61; 422/939; 436/165; 436/901
[58] Field of Search ................................ 422/59, 58, 56, 422/61, 939; 436/169, 165, 810, 901

[56] References Cited

U.S. PATENT DOCUMENTS

| | | | |
|---|---|---|---|
| 4,981,786 | 1/1991 | Dafforn et al. | 33/535 |
| 5,145,789 | 9/1992 | Cortie et al. | 33/548 |
| 5,256,372 | 10/1993 | Brooks et al. | 422/58 |
| 5,504,013 | 4/1996 | Senior | 436/165 |
| 5,611,995 | 3/1997 | De Zoeten et al. | 422/58 |
| 5,881,596 | 3/1999 | Tsuji et al. | 73/426 |
| 5,962,215 | 10/1999 | Douglas et al. | 435/4 |

*Primary Examiner*—Maureen M. Wallenhorst
*Attorney, Agent, or Firm*—Robert M. Downey, P.A.

[57] ABSTRACT

The device includes a housing having a main body including an analysis chamber with at least one chemical reagent composition contained therein and a vessel portion for receiving and capturing a fluid specimen taken from a beverage. The device is structured to transfer the captured fluid specimen from the vessel portion to the analysis chamber wherein the chemical reagent composition, when exposed to the fluid specimen, performs a visible presumptive color assay to determine whether undesirable substances, such as fulnitrazepam, sodium gamma hydroxybutyric acid or caffeine, are contained in the beverage. One or more windows are provided on the housing for viewing the results of the visible presumptive color assay. The fluid specimen and one or more chemical reagent compositions remain contained within the analysis chamber to prevent contamination of the beverage as well as tampering with the captured fluid specimen.

19 Claims, 6 Drawing Sheets

BEVERAGE ANALYSIS SAMPLE

BACKGROUND OF THE INVENTION

1. Field of the Invention

The analysis device for beverages described herein relates generally to a covert apparatus that uptakes a liquid sample for analysis. More particularly, the invention relates to a beverage analysis device that extracts a liquid sample from a beverage by capillary forces, and subjects the sample to an analytical system that performs a visible presumptive color assay.

2. Description of the Related Art

In the technical field of chemistry it is known that as a means for analyzing fluids of varied types, liquid samplers and reagent strips have been developed. Currently analytical liquid samplers and test strips are used in area's that include medicine, drug detection, water quality, industrial pollutants and in the environmental arena.

Diverse types of liquid samplers and reagent test strips are known to the art. Outgrowth of such devices for the rapid identification of varied chemical substances at different levels of saturation in many types of liquid and biological samples are apparent to all versed in the art. Such embodiments are known for assays of water, solvents, blood, and many more additional fluid samples. The majority of these devices are handled by individuals with at least some skill level and understanding relating to their specific field of endeavor.

The analysis is documented primarily by visual means. However, lab facilities and portable instrumental methods can be employed. Efficient, accurate, portable and economical liquid samplers and test strips have an advantage over the more complicated and expensive instruments.

As unfortunate as it may seem, there has become an urgent need to test all types of beverages for different substances due to the devious and criminal mindset of certain individuals in today's society. It is mankind's indifference to placing himself/herself in jeopardy that has set a stage for such an invention.

The recent onslaught of "Date Rape" compounds placed in the beverages of unsuspecting individuals is not only despicable and disgusting, but truly dangerous to the individual ingesting the substance. As insidious and perilous as this may sound, the dangers do not stop here. In addition to the worries of unprotected sex, compounds such as GHB (known generically as gamma hydroxybutyric acid) and ROHYPNOL, when mixed with alcohol or other drugs, may lead to respiratory depression, aspiration, and even death. These compounds produce a sedative effect, amnesia, muscle relaxation, and a slowing of psychomotor responses. The pharmaceutical ROHYPNOL is widely known to the masses as "roofies", "ruffles", "roche", "R-2", "rib", and "rope" and reportedly is quickly becoming the "date rape drug of choice."

ROHYPNOL is a pharmaceutical known by the generic name flunitrazepam (a benzodiazepine). Evidently, it is a very potent tranquilizer, and similar in nature to VALIUM (diazepam) but apparently many times stronger.

Sedation occurs 20–30 minutes after administration and lasts for several hours. The drug is often distributed on the street in it's original "bubble packaging" which adds an air of safety to the drug at time of purchase. When taken time and time again, it can lead to physical and psychic dependence which is thought to increase with both dose and duration of use.

Police departments in several parts of the United States of America, have reported that, after the ingestion of ROHYPNOL several young women have reported waking up in fraternity houses with no clothes on, finding themselves in unfamiliar surroundings with unfamiliar people, or having actually been sexually assaulted while under the influence of the drug.

Recent seizures and anecdotal reporting indicate that distribution and abuse of flunitrazepam are increasing among young people domestically, even though the drug is neither legally sold or manufactured in the United States.

Sodium Gamma Hydroxybutyric (GHB), a patented pharmaceutical, is also causing alarm. The clinical uses of GHB range from drug addictions to eating disorders and numerous other afflictions. However, it is also being abused in similar fashions to that of (ROHYPHOL). The substance GHB is a endogenous compound that induces absence-like seizures and provides sedative effects similar to that of flunitrazepam (ROHYPHOL). While it is not presently available in tablet form, that most assuredly will change. Overseas manufactures have recently been granted patent protection in the United States for a time release tablet form of this substance.

Reportedly GHB has sustained usage, and with the advent of a more functional and readily available tablet, a resurgence of GHB will probably occur. At this time, the substance GHB is not under the control of the United States Food and Drug Administration and is presently available for purchase over the Internet.

Reports of individuals purposely ingesting the substance GHB combined with alcohol, are dying or being subjected to unrelenting comas. Additionally, random individuals unknowingly are being subjected to having their lives and health being jeopardized by slight of hand cowardly perpetrators.

These drugs when placed in an unsuspecting individuals beverage and consumed, leave the victim highly venerable to crimes such as robbery, rape, death, and assault. It has been reported that even human organs have been stolen in this manner in distant third world countries. The perpetrators of these crimes are from all walks of life, making this problem all the more disconcerting.

Furthermore, the broadcasting of such acts in the news media raises the consciousness of individuals, regarding the methods and means that are available to the perpetrators. Unfortunately, this can also create copycat incidents. Since the drugs are readily available, a strategy and device must exist for deterrence. The device of the present invention provides a precautionary routine to the users of the device, which substantially reduces the likelihood of becoming a victim of such crimes.

Caffeine, on the other hand, presents a different concern. The rise in consumption of decaffeinated beverages has resulted in part from the health concerns of ingesting excessive amounts of caffeine. Caffeine, a partially water-soluble alkaloid, stimulates the central nervous system. Excessive amounts of caffeine can make people tense, irritable, unable to sleep, and, in some cases, elevate the heart rate to unsafe levels. Caffeine can also irritate the alimentary canal. It is common for people diagnosed with sensitive stomachs and colons, as well as other medical conditions, to be required to refrain from ingesting caffeine as part of their medical treatment. Also, an individual requesting a decaffeinated beverage can not be fully certain of the reduced level or absence of caffeine in the beverage.

It has become evident, that in this day and age, consumption of beverages of various types presents a significant danger and, without prior testing (just prior to consumption), there is a definite risk to ones health and safety.

The related art is crowded with test devices for a wide variety of liquid substances, the following of which are examples of the most relevant developments. As shown and described in U.S. Pat. No. 3,965,750 a liquid sampler is provided, comprised of an elongated tube having a fluid-holding well cap.

A liquid sampler as shown and described in U.S. Pat. No. 3,994,170 provides a device with a collecting container, supplied with a slot shaped aperture in the outer wall. The device includes a spiral rotating inner wall assembly that opens or closes said aperture.

As exemplified in U.S. Pat. No. 4,157,664 a device with two telescopically disposed receptacles, forms a closed container.

In U.S. Pat. No. 4,625,574 a method and apparatus are disclosed for obtaining a field sample. Furthermore, a method and means for sealing said sample from deterioration, additional contamination, or loss of volatile components are provided.

In U.S. Pat. No. 5,583,044 a fluid sampler and testing unit is exemplified. This device performs a presumptive brilliant chromophoric test.

In U.S. Pat. No. 5,728,076 a ampoule holder and actuator is shown and described. The device includes a cylindrical ampoule and a handle with a bore for receiving a piston.

An apparatus with provisions for a test strip, is disclosed in U.S. Pat. No. 5,611,995. The device detects a specifically reacting substance in a liquid, and is intended for home use or by nonprofessional organizations, whereby the test is usually carried out by laymen or non-skilled people.

Also known to the art, and as exemplified in U.S. Pat. No. 3,915,639 is a drug of abuse dipstick, useful in visually identifying an ion exchange in physiological fluids. A dipstick is provided in combination with a stain- producing reagent, impregnated on a substrate within a matrix of numerous ion exchange resins that are outwardly exposed to the fluid to be tested.

An immersible test strip including a wick member enclosed in a fluid impervious sheath, and an aperture exposing a portion of the wick member, is illustrated by U.S. Pat. No. 4,092,115.

Also known in the art, as exemplified by U.S. Pat. No. 3,715,192 to Wenz et al, is an indicator strip useful in analytical chemical procedures. The main advantage of the construction of this device is that the capillary material which absorbs the liquid medium allows the sample to be examined quickly, thereby preventing chromotographic separation of the reagent during the absorption of the liquid media.

Despite the vast number of devices and systems for sampling and/or analyzing various fluids which have been proposed in the related art, the urgent need for the present invention has not been fulfilled.

Presently, there remains a definite and unfulfilled need for an apparatus that provides a safe method and effective means for detecting specific substances in beverages ingested by humans.

In particular, there is a need for a beverage analysis device which, when packaged, will remain sterile. The device needs to be simple to handle and operate, while providing a proficient and explicit detection utilizing color assays. The beverage analysis device should be easy to conceal and conveniently remain undetected if necessary, while being able to perform the analysis with no additional technical apparatus. A disguised appearance similar to that of a common object could be useful in certain circumstances. Additional requirements of the apparatus are safe disposal and moderate cost to the public.

SUMMARY OF THE INVENTION

The device of the present invention provides secure atmospheric and leak resistant chambers structured within the assembly, and uses the scientific laws underlying the workings of natural phenomena and mechanical processes associated with the fundamental principles of solid phase extraction, capillary column chromatography, thin layer paper chromatography and ion exchange.

The devices in the several embodiments are used to produce accurate single or multiple qualitative and semi-quantitative color assays in order to detect the presence of specific substances in fluids, and particularly to varied beverages ingested by humans such as, but not limited, to soda, fruit juices, alcoholic punches, cocktails, beer, even and tonic water.

The invention is particularly suited for analyzing beverages that can be adulterated with known and specific compounds such as, but not limited to, the pharmaceuticals: Sodium Gamma Hydroxybutyric Acid, known generically as GHB; and Flunitrazepam, known generically as ROHYPNOL. Furthermore, the invention can be used to analyze beverages where the substance 1,3,7 Trimethylxanthine, known as Caffeine, is provided at fluctuating levels of concentration.

The device of the present invention, in accordance with the several embodiments thereof, is useful for personal safety and guardianship when there is a concern about the presence of dangerous and/or unhealthy substances in one's beverage.

The present invention is directed to a sampler device for random analysis of beverages just prior to consumption in order to determine whether certain undesirable substances are contained in the beverage. Once removed from the sterile packaging, the devise is prepared for immersion within the beverage and retrieval of a fluid specimen. This is handily accomplished by pulling apart geometrically opposed telescoping assemblies. One assembly augments the devices length by becoming a locked open support member, while also revealing a viewable colorimetric window. The assembly serves as a vessel to uptake the fluid specimen; exposing previously concealed apertures. In use, the device is immersed in the beverage and uptake of a fluid sample occurs. After removal from the beverage, closure and sealing of the device is accomplished by applying pressure to a pressure application surface on the vessel. When locked closed, an internal mass of the vessel is then rotated axially. The internal mass comprise an internal seal affixed to a reagent ampoule. The fluid specimen then migrates, by capillary forces, into the ampoule and a presumptive color assay is performed.

Accordingly, with the foregoing in mind, it is a primary object of the present invention to provide a beverage analysis sampling device that performs qualitative and semi-quantitative presumptive color assays, for the detection of Sodium Gamma Hydroxybutyric Acid (GHB) ROHYPNOL and concentrations of Caffeine that may be present in a beverage.

It is a further object of the present invention to provide a beverage analysis sampler, wherein the assembly includes a vessel, a centered mass within the vessel, a analysis chamber, apertures, an o-ring seal, a support member, a sealed reagent ampoule and functional chemistry.

It is still a further object of the present invention to provide a beverage analysis sampler with a lock means for permanent locking engagement between the vessel and the analysis chamber when the vessel is in the locked closed position.

It is yet another object of the present invention to provide a beverage analysis sampler, as set forth above, wherein the assembly includes means for compromising the seal of the reagent ampoule when the vessel is in the locked closed position.

It is a further object of the present invention to provide a beverage analysis sampler with a seal means for permanent sealing engagement between the vessel and the analysis chamber when the vessel is in the locked closed position and means for preventing release of the captured specimen and functional chemistry, thereby preventing hazardous exposure to the functional chemistry and/or contamination of the beverage.

It is yet another object of the present invention to provide locking engagement between the support member and the analysis chamber when the support member is in the locked open position.

It is still a further object of the present invention to provide a beverage analysis sampler shaped and configured to provide a covert identity to that of a cigarette, and wherein the sampler is capable of a single and/or multiple unit packaging.

It is yet a further object of the present invention to provide a beverage analysis sampling device for personal use without requirements such as: extensive training; advanced motor skills; or expensive lab facilities.

It is still a further object of the present invention to provide a beverage analysis sampler which is relatively inexpensive to manufacture and which, therefore, can be sold at a retail price suitable for adolescents and young adults to purchase.

The objects and advantages of the present invention are further achieved in alternative embodiments, within the spirit and scope of the invention, including an analytical test strip which detects the presence and concentration levels of Sodium Gamma Hydroxybutric Acid (GHB), ROHYPNOL and Caffeine in beverages. Once removed from the sterile moisture resistant packaging, the test strip is immersed into the suspect beverage. The liquid sample is absorbed through an aperture into the analysis chamber via a wick assembly. Capillary forces at work absorb a sufficient charge of the liquid sample beyond a membrane which prevents back flow of the sample into the beverage. Specific reagent complexes are embedded within the analysis chamber upon or juxtaposed to said wick. The analysis chamber and wick provide sufficient capacities to complete their objective. Construction of the analysis chamber provides a transparent embrasure for viewing the presumptive color assay being performed within.

Accordingly, with the foregoing in mind, it is a primary objective of the additional embodiments to provide plausible variations to the beverage analysis sampler exemplified herein.

It is a further object of the present additional embodiment to provide a test strip produced of two independent polymer layers bonded together to form a flexible support and analysis chamber in the test strip.

It is still a further object of the present additional embodiment to provide a test strip with an aperture for uptake of a fluid specimen and into communication with the analysis chamber.

It is yet another object of the present additional embodiment to provide a test strip with a membrane structured and disposed to prevent back flow of the captured fluid sample and chemical reagents within the analysis chamber, thereby preventing hazardous exposure to and/or contamination of the beverage being analyzed and subsequently consumed.

It is a further object of the present additional embodiment to provide a test strip with a transparent window for color observation of the analysis within the analysis chamber.

It is still a further object of the present additional embodiment to provide a test strip assembly capable of single or multiple unit packaging, and which is structured to provide simplicity of use, while also providing a very inexpensive means for personal safety.

In the drawings and in detailed description of the invention that follows, there are essentially shown and described only preferred embodiments of this invention, setting forth what is considered to be the best mode contemplated of carrying out this invention at this time. As will be realized, this invention is capable of other and different embodiments, and it's several details are capable of modification in various respects, all without departing from the spirit and scope of the invention.

Accordingly, the drawings and the detailed description are to be regarded as illustrative in nature, and not as restrictive.

BRIEF DESCRIPTION OF THE DRAWINGS

Reference is now made to the accompanying drawings, which forms a part of the specification of the present invention.

FIGS. 7A–7B illustrate, in isolated cross-sectional views, the seal means and lock means between the analysis chamber and support member of the sampler device;

FIGS. 16A–16B are perspective views of a multiple unit attachment and package means for packaging multiple units of the sampler in accordance with a preferred embodiment thereof;

FIGS. 20A–20B illustrate, in plan view, a folding sequence to reduce the overall length of the strip for packaging;

Like reference numerals refer to like parts throughout the several views of the drawings.

The novelty, advantages and range of usefulness of the preferred embodiments of the invention will become better understood in the following detailed description of the invention.

DETAILED DESCRIPTION OF THE INVENTION

The present invention is directed to a beverage analysis sampler for detecting the presence, and in sum instances the level, of certain substances which may be contained in a beverage.

Particularly beneficial applications of the invention include analysis of varied alcoholic and non-alcoholic beverages under suspicion of Sodium Gamma Hydroxybutric Acid GHB or ROHYPNOL adulteration. Additionally, the invention is useful to perform quantitative analysis of caffeine levels in various beverages including soft drinks, coffee and tea.

Figure 1:
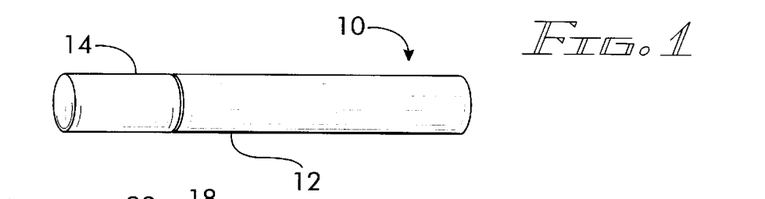
FIG. 1 is a perspective view of a preferred beverage analysis sampler in accordance with the present invention, shown in a collapsed position for packaging and carrying prior to use.

Referring to several views of the drawings, and initially to FIGS. 1–16-B, a first preferred and practical embodiment of a beverage analysis sampler is shown, generally indicated as 10. Referring to FIG. 1, it can be appreciated that the beverage analysis sampler, according to the first preferred embodiment thereof, visually resembles a cigarette. If the sampler were to be of white color and sized accordingly, an individual might not be aware that it is, in fact, not an actual cigarette until the person handles the object. Accordingly, this resemblance has a covert value in certain situations. The first preferred embodiment, as depicted in the several views, includes a main body 18 a vessel cover 14 and a support member 12 slidebly maintained on opposite respective ends of the main body. The vessel cover 14 and the support member 12 are specifically structured to move, in telescoping relationship to the main body from a collapsed position to an extended or open position. As is readily apparent, if necessary or desired, the beverage analysis sampler 10 can be longitudinally shaped in additional geometric shapes other than round, such as square, rectangular, oval and the like and yet, retain the ability to have telescoping assemblies.

Referring to FIGS. 1–5 of the drawing, the preferred beverage analysis sampler 10 presently provides inherent design criteria novel to such an application. Provisions in structural design, of the sampler device 10 implement and incorporate modern manufacturing processes, providing the end user with a device that is safe, economical and accurate in the detection of suspect substances in one's beverage. Specific structures of the preferred embodiment are manufactured by injection molding, thereby affording substantial quantities of parts within the dimensional guidelines specified, at very reasonable cost. Specific assemblies of the beverage analysis sampler 10 are designed to be constructed of white opaque plastic materials which the United States Food and Drug Administration FDA has validated to be safe for use with food and beverage consumption.

Although, the apparatus shall visually appear to have been manufactured of like materials, the structural differences between assemblies of the preferred beverage analysis sampler 10 may demand usage of more than one type of plastic. Materials such as, but not limited to, polyethylene terephthalate (a polyester material) provides a maximum continued use temperature of 230° degrees Fahrenheit, excellent wear resistance, superior dimensional stability, low coefficient of friction, very good chemical resistance, low moisture absorption and is FDA approved for food contact. Additionally, Nylon 6/12 and Nylon 6/6 provide a maximum intermittent temperature use range to 355° degrees Fahrenheit, have excellent dimensional stability, withstand moisture absorption, have high strength with a low coefficient of friction, resist most common chemicals and meet FDA approval including FDA 21 CFR (177.1500) and MIL M-20693, Type III, Grade E. Additional material considerations for the manufacture of the beverage analysis sampler 10 include the following: Polyetherimide (ULTEM); Ultra-High Molecular Weight Polyethylene (UHMW); Acetel homopolymer material (recognized commercially as DELRIN); and polycarbonate.

Referring again to FIGS. 1–5, the beverage analysis sampler 10 includes the main body 18 concealed within the two telescoping assemblies, namely the vessel cover 14 and the support member 12. Providing concealment of the main body 18 by the vessel cover 14 and the support member 12 affords the apparatus the novel disguise, additional structural strength and reduced packaging length. The support member 12 is provided with a telescoping action by means of a longitudinally concentric bore dimensionally congruent to the main body 18. As seen in the several views in the drawings, the vessel cover 14 is geometrically opposed to the support member 12. Conveniently, vessel cover 14 is also provided with telescoping action by a means of a longitudinally concentric bore dimensionally congruent to the main body 18.

With continued reference to FIGS. 2–5, the main body 18 includes a vessel portion 20 and an analysis chamber 16. The vessel portion is provided with at least one aperture 28 which passes through the structural walls of the vessel portion 20 at a predetermined location. The shape, and placement of the aperture 28 will become clear with continued reference to the detailed description. Conveniently, the aperture 28 provides for the uptake of a fluid sample and affords fluid communication into the vessel interior chamber 22 of vessel portion 20. An o-ring 30 around the exterior of the main body 18 in a predetermined position becomes a means for sealing vessel cover 14 about the main body 18 and in covering relation to the aperture (s) 28, to thereby capture the fluid sample within the interior chamber 22. The placement of the o-ring 30 will become clear with continued reference to the detailed description and FIGS. 2–5.

Figures 2, 3, 4:
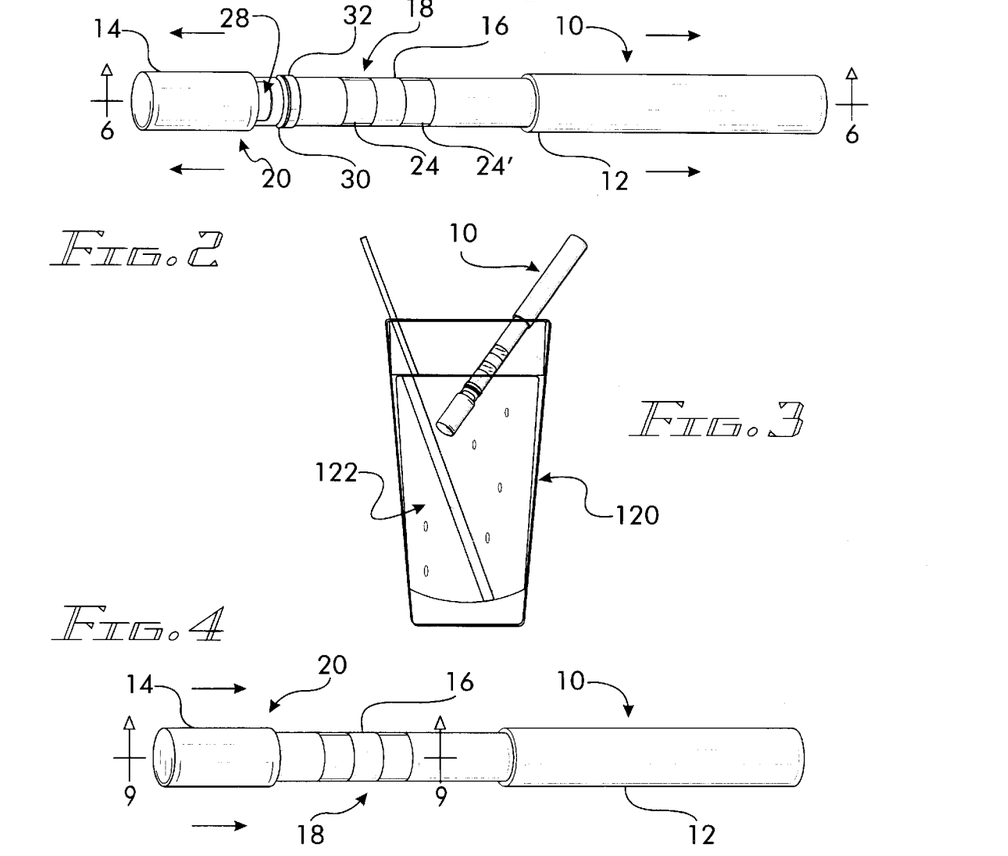
FIG. 2 is a perspective view of the beverage analysis sampler of FIG. 1, in the open position for obtaining a fluid sample to be analyzed.
FIG. 3 is a perspective view of a the beverage analysis sampler as depicted in FIG. 2, inserted into a beverage.
FIG. 4 is a perspective view of the beverage analysis sampler of FIG. 1, in the locked closed and sealed position after having captured a fluid sample from a beverage.

In use the device, as depicted in FIG. 3, is inserted into a tumbler of beverage and, when swayed back and forth briskly or in a simulated stirring motion, will elevate any air pockets within the vessel interior chamber 22. Once the purposeful uptake of suspect fluid is accomplished, applied pressure against vessel cover 14 toward the analysis chamber 16 seals vessel cover 14 at the o-ring 30 juncture.

Lock means associated with the telescoping vessel cover 14 and support member 12 is described in more detail hereinafter with reference to FIGS. 6A–6C, 7A–7B and 8 of the drawings.

Figure 5:
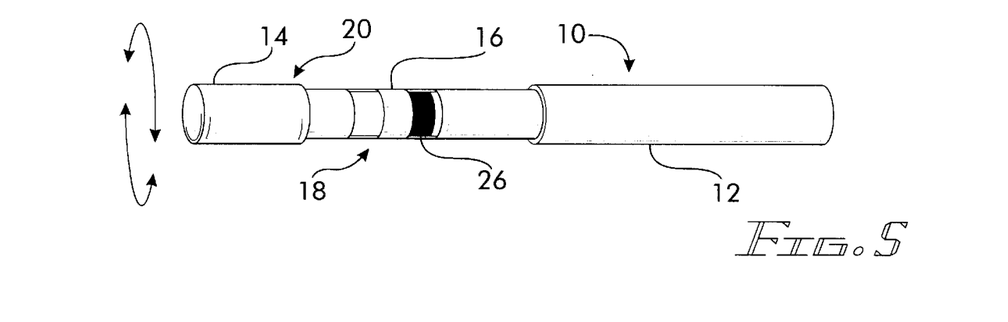
FIG. 5 is a perspective view of a preferred beverage analysis sampler as depicted in FIG. 4, illustrating vessel rotation and visual conformation.

With continued reference to FIG. 5, after the uptake of the suspect fluid is accomplished, and the action of sealing the apparatus is completed, turning of vessel cover 14 a minimum of 90° degrees compromises an internal seal affixed to a reagent ampoule previously installed within the analysis chamber 16, and a presumptive color assay 26 is performed. The simultaneous visual results will be seen through the optical embrasures 24 and/or 24' located within the analysis chamber 16.

The presumptive color assay for ROHYPNOL will be seen through embrasure 24. The recorded color change from white to a violet/purple color occurs (if present) within 30 seconds or less. If a violet/purple color does not appear in embrasure 24 within 30 seconds, the beverage analysis should be considered negative for ROHYPNOL (a ketobenzodiazepine).

The presumptive color assay for GHB will be seen through embrasure 24'. The recorded color change from white to a yellow/orange color or a purple/black color also occurs within 30 seconds or less. If a yellow/orange color appears within 30 seconds or less, the beverage analysis should be considered negative for GHB. However, if a purple/black color appears within 30 seconds or less, the beverage analysis should be considered suspect for the presence of GHB.

As seen in the drawings, the GHB indicator embrasure 24' is the furthest embrasure from the end of the apparatus described as, vessel portion 20. As mentioned previously, the GHB indicator provides visual color conformation with or without the presence of GHB. This conveniently provides the individual using the beverage analysis sampler with assurance that he/she has utilized the device correctly.

The specifics of the ampoule, ampoule seal and varied chemical compositions within the ampoule will become known with continued reference to the detailed description.

Referring now to FIGS. 6A–6C, 7A–7B and 8, in accordance with the present invention, the preferred beverage analysis sampler 10 was designed for personnel safety. It, therefore, must be absolutely safe for an individual to use no matter how skilled or intelligent he/she may or may not be. The use of chemical reagents must be addressed and made to be a moot point. In accordance with the present invention, additional means for the users personal safety have been addressed by affording this device with internal stops, seals, and lock means.

Figure 6:
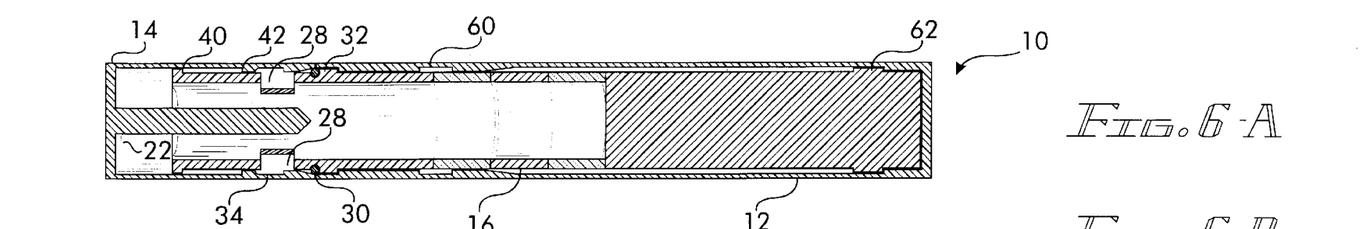
FIGS. 6A–6C illustrate, in sectional view, along the plane indicated by the line 6—6 in FIG. 2, the telescoping sections and their lock means.
Figures 6, 7, 8:
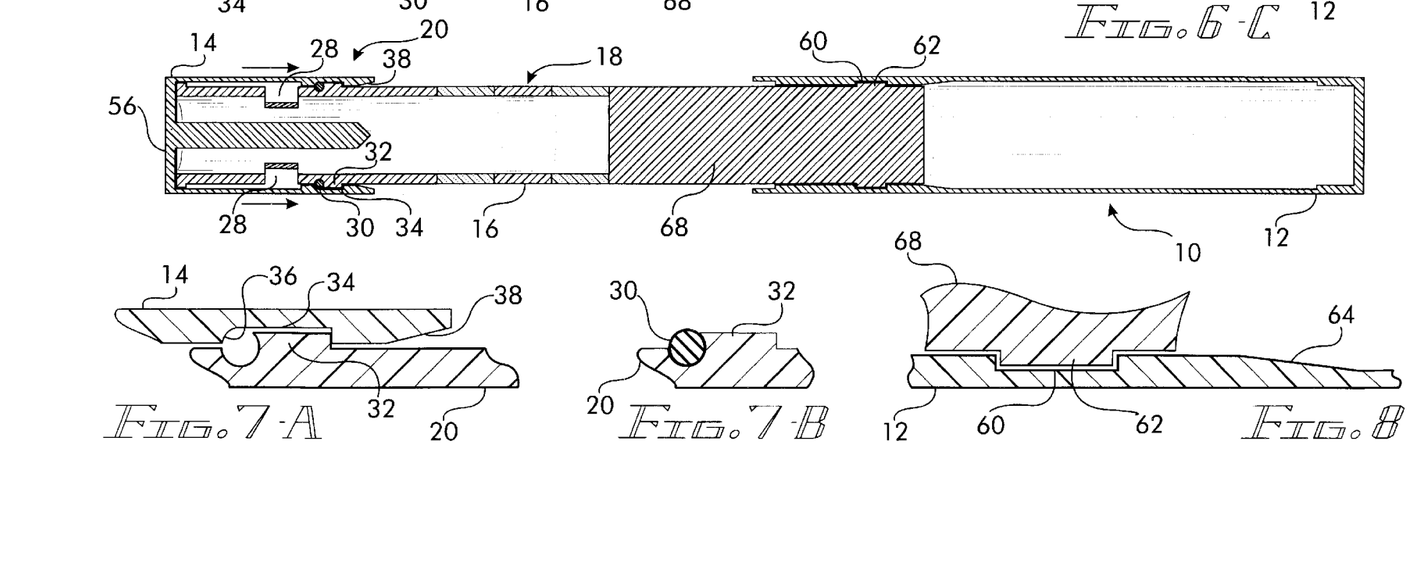
FIG. 8 is an isolated exploded view of the lock means for the support member.

As may be readily appreciated with reference to FIGS. 6A–6C, support member 12 has (2) two positions, closed and locked open. The closed position, as shown in FIG. 6A, is when the apparatus is packaged and/or the analysis chamber 16 is hidden from view. The locked open position, as shown in FIGS. 6B–6C and 8, is when the telescoping action of support member 12 is applied to the device, thereby exposing the analysis chamber 16. In the locked open position, lock member 60 of support member 12 engages lock member 62 of the main body extension 68. Telescoping outward movement of support member 12 causes the internal incline plane 64 of support member 12 to exert pressure onto the opposing surface of lock member 62, resulting in outward expansion of the diameter of support member 12 to a point that lock member 62 of has enough clearance into lock member 60. In the locked open position a shoulder of lock member 60 abuts a shoulder of lock member 62, thereby permanently retaining lock member 62 within the confines of lock member 60.

As may be readily appreciated, vessel cover 14 has (3) three positions, closed, open and locked closed. The closed position, as shown in FIG. 6A, is when the apparatus is packaged and the aperture 28 is hidden from view. The open position as shown in FIG. 6B, results when vessel cover 14 telescopes away from the analysis chamber 16, thereby exposing the aperture 28. Additionally, stop 40 of the vessel portion 20 is engaged by stop 42 of vessel cover 14. After manufacturing, the previously mentioned stops do not allow separation of vessel cover 14 from the vessel portion 20. The locked closed position, as shown in FIG. 6C and 7A, is when vessel cover 14 is forced toward the analysis chamber 16 by applying force upon the pressure application surface 56 of vessel cover 14 and, after the internal incline plane 38 of vessel cover 14 encounters and passes over the o-ring 30, the internal incline plane 38 then encounters the lock member 32 of vessel portion 20. With applicable force, the circumference of vessel cover 14 expands to a degree sufficient to cause engagement of lock member 34 of vessel cover 14 with lock member 32 of vessel portion 20. The locked closed position is contingent on the geometry of the internal incline plane 38 exerting enough relative pressure onto the opposing surface of lock means 32, to thereby cause outward expansion of the diameter of vessel cover 14 to a degree that lock member 32 has sufficient clearance to rest within lock member 34. The abutting shoulders of lock member 34 and 32 permanently retain lock member 32 within the confines of lock member 34.

A liquid tight seal for vessel portion 20 is achieved using this design when specific dimensions are taken into account. As depicted in FIG. 7A, reference is made to structural and dimensional characteristics of shape 36. Shape 36 corresponds to the outside diameter of o-ring 30 and accounts for a form fitting rate of compression of o-ring 30 relative to the pressure exerted upon it. When in the locked closed position, continual pressure is exerted onto o-ring 30 by shape 36 of vessel cover 14 by a means directly related to the longitudinal dimensions of lock member 34. As shown in FIG. 7B, the o-ring 30 is mounted within an edge of lock member 32. The contoured channel formed in the lock member 32 provides a structural support behind the o-ring 30 when the internal incline plane 38 of the vessel cover 14 forcibly engages the o-ring 30 and lock member 32 of the vessel portion 20.

Figure 9:
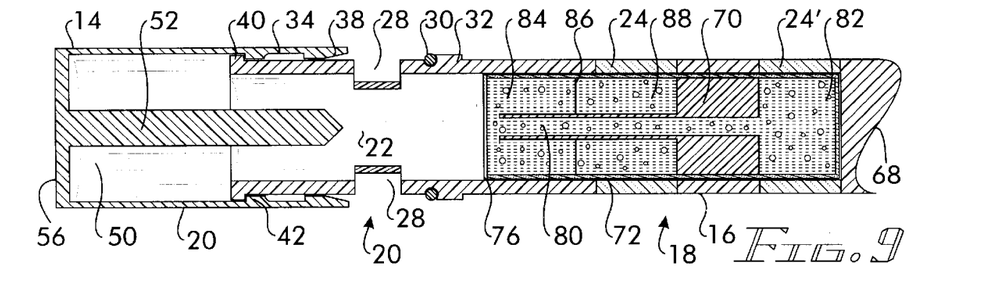
FIGS. 9 and 10 are isolated sectional views taken along the plane indicated by the line 9—9, in FIG. 4, illustrating the vessel in the open and sealed positions, respectively.
Figure 10:
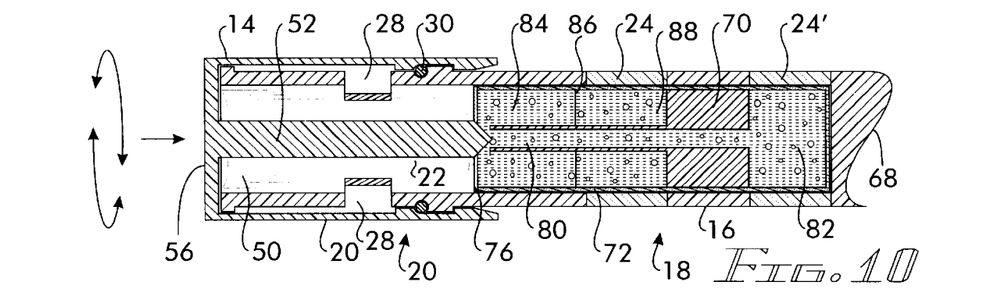

As best seen in FIGS. 9–10, the apertures 28 are depicted in the exposed and contained position. As is readily apparent, the centers of the respective apertures are 180 degrees apart on the circumference of the vessel portion 20. The apertures are defined by openings formed through the wall of the vessel portion 20, to thereby provide fluid flow into the cavity 50. While the apertures are shown to be rectangular, other shapes such as one or more equally spaced oval, round, rectangular, oblong, square openings are obviously suitable. The aperture 28 is proportioned to the diameter of the analysis chamber 16 to avail the interior of the device exposure to sample and yet retain sufficient material between apertures so as not to weaken the structural integrity of the chamber wall. The apertures are sized and shaped to relieve atmospheric pressure and to supply enough fluid specimen to rapidly fill cavity 50 of the vessel interior chamber 22.

Referring again to FIGS. 9 and 10, the analysis chamber 16 is shown encapsulating an ampoule 72 manufactured to exacting specifications of borosilicate glass. Recognized by trade names such as PYREX and SCHOTT glass, borosilicate glass is impervious to most chemicals, except hydrofluoric acid, hot phosphoric acid, and hot caustics. Additionally, the transparent glass has a high heat tolerance and provides optical clarity.

If the prepared ampoule is not injection molded within the analysis chamber 16, then installation of the ampoule 72 is accomplished prior to the vessel 14 being installed during the manufacturing process. It is then necessary to affix the ampoule 72 within the analysis chamber 16 by correctly placing a droplet of an adhesive onto the outward surface of the glass end of the ampoule 72 which is not bound with the penetrable seal 76. Recommendations for the adhesive are "instant adhesives" such as cyanoacrylates, anaerobics, silicones, contact cements, urethanes, acrylics and even hot melt. Although, the application demands a calculated specific thinness the dimension is readily attained. The glass ampoule 72 is then evenly pressed into the concentric bore of the analysis chamber 16 until the ampoule 72 engages with the base of the bore, resulting in a permanent foundation.

The application of heat without adhesives to the analysis chamber 16, after the insertion of the ampoule 72, is also an option. Controlled heating will result in the seizing of the ampoule within the bore. Care must be taken to retain the concentric dimensions. The option of a press fit can also be entertained, but absolute control over the dimensions is needed. The depth of the analysis bore in relation to the length of the ampoule 72 are in direct correlation to the lock member 32 of the vessel portion 20. The ampoule 72, is seated within the analysis chamber 16 so that the ampoule seal 76 is longitudinally aligned for engagement with the seal puncturing member 52 of the vessel cover 14 when forced into the aforementioned, closed locked position.

Figure 11:
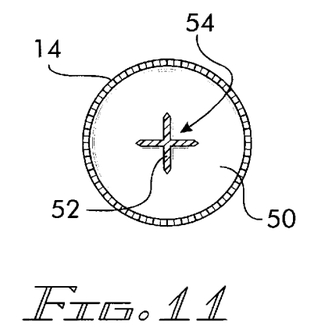
FIG. 11 is a sectional view taken along the plane indicated by the line 11—11 in FIG. 12, illustrating a seal punctuating member in the vessel of the invention.
Figure 12:
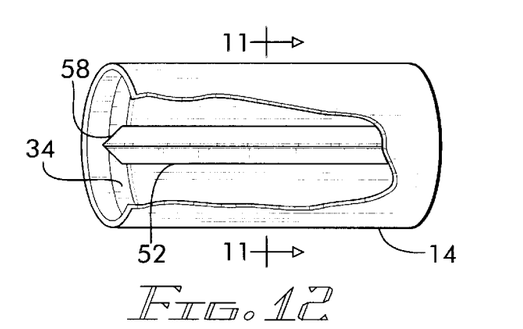
FIG. 12 is a perspective view of the vessel, as depicted in FIG. 1, shown in cut-away to reveal the seal punctuating member therein.
Figure 13:
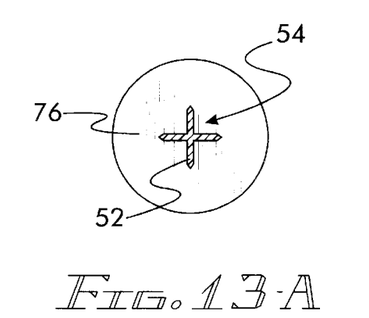
FIGS. 13A–13B illustrate, in isolated view, a sequence of engagement and penetration of the ampoule's seal means by the punctuating member within the vessel.

Referring now to FIGS. 11 and 12, vessel 14 is shown with a seal punctuating member having a cross shape when viewed in cross section as in FIG. 11. The two longitudinally intersecting plans of the seal punctuating member are injection molded within the vessel cover 14, and attached adjacently to the interior surface of the vessel cover 14. Contour molded at the opposite end to a 45° degree angle affords a piercing surface 58 structured and disposed for penetration of the ampoule seal 76. Conveniently, the surface area generated by this design allows for narrow, yet rigid incisors.

With additional reference to FIGS. 13A and 13B, once pressed through the ampoule seal 76, rotation of the vessel cover 14 enlarges the opening, dramatically illustrated as expansion 77 in FIG. 13B. The volume of specimen contained within cavity 50 of vessel cover 14 and the vessel interior chamber 22 is not impaired by this structure. The elongated seal punctuating member 52 is conducive to fluid flow, allowing the fluid specimen to travel within the punctured area of the ampoule seal, illustrated as area 54.

The penetration of the ampoule seal 76 by the seal punctuating member 52, concurrently with engagement of the lock member 34 of the vessel cover 14 with lock member 32 of the vessel portion 20, provides a safer means for containing the chemical reagents within the interior of the sampler 10, thereby preventing contamination of the beverage, potential poisoning or tampering with the internal chemical reagents and captured fluid specimen.

Referring again to FIGS. 9 and 10, and in addition the FIGS. 14A–14D, the glass reagent ampoule 72 of the preferred embodiment includes an ampoule partition 70, as well as reagent complexes. The reagent complexes are indicated as GHB reagent 80 and ROHYPNOL reagent 84. The reagent flush zones are indicated as GHB flush zone 82 and ROHYPNOL reagent flush zone 88, also indicated is ampoule seal 76. The ampoule partition 70 is a injection molded, tubular assembly as shown in FIG. 14A, comprising an outer most diameter sized to press fit within the inner diameter of the glass reagent ampoule 72 and structured to segregate the inner confines of the reagent ampoule 72. The ampoule partition 70 also includes an elongated straw element 78 having a hollow core 74 which provides fluid passage from one side of the ampoule partition 70 to the other.

Figure 14:
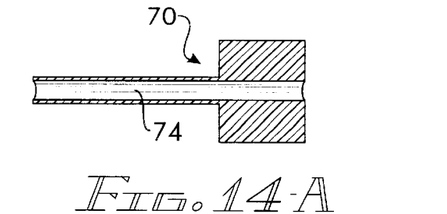
FIGS. 14A–14D illustrate, in isolated sectional view, a sequence of assembly of the component elements of a segmented ampoule in accordance with the embodiment of FIG. 1.

A packing sequence for the construction of a reagent ampoule 72 developed to perform a presumptive color assay for detection of GHB and/or ROHYPNOL in beverages is illustrated in FIGS. 14B–14D. A GHB flush zone 82 made up of absorbent is packaged first. Applicable compositions of absorbents comprise micro-crystalline cellulose of a fibrous and/or micro-granular power. A packing of silica media or fibrous material similar in structure and composition to WHATMAN filter paper number # 4 may be used. The ampoule partition 70 is now installed within the reagent ampoule 72. The GHB reagent 80 is packed within the elongated hollow core 74 (See FIG. 14-C) of the straw 78, extending through the ampoule partition 70. The GHB reagent 80 is constructed of rolled or packed fibrous material, packed cellulose and/or silica. The indicator, 5,5'-Dibromo-o-cresolsulfonphthalein has been impregnated within the rolled or packed substrate via an ethanol solution. A portion of the impregnated, dried filter paper is loosely rolled and implanted within the hollow core 74 of the ampoule partition. The length of the rolled impregnated filter paper is sufficient to provide fluid contact at the exposed ends of the hollow core 74. A ROHYPNOL flush zone 88 made up of an absorbent material saturated with the indicator potassium hydroxide is then packed within the ampoule. Suitable compositions of absorbents comprise micro-crystalline cellulose of a fibrous and/or micro-granular powder. A packing of silica media or fibrous material similar in structure and composition as WHATMAN filter paper number # 4 may also be used. A layer of filter paper 86 is then inserted into the ampoule to form an absorbent partition. Additionally, a reagent zone 84 is made up of absorbent material saturated with methanolic 2,4-dinitrobenzene and packed within the ampoule. Suitable compositions of absorbents comprise micro-crystalline cellulose of a fibrous and/or micro-granular powder. Again a packing of silica media or fibrous material similar in structure and composition as WHATMAN filter paper number # 4 may be used. The open end of the reagent ampoule 72 is then closed with a seal 76.

Referring again to FIGS. 13A and 13B, the seal 76 is a self-adhering foil with a thickness range of between 0.001–0.009; a thickness of 0.005 being particularly useful. The foil after being pierced by the seal punctuating member 52, is then moved aside when the seal punctuating member 52 is rotated, thereby enlarging the pierced opening 77 through the seal 76 and increasing exposure of the absorbents. Additionally, the seal 76 can be produced of a stretched micro thin polymer membrane bonded to the ampoule. The micro thin polymer type of seal, having been stretched to the outer circumference of the glass or polycarbonate ampoule, is then chemically and/or thermally bonded. It will automatically recede outwardly when pierced in the center by the seal punctuating member 52, thereby exposing the absorbents.

The following example illustrates the purposeful preparation and/or combinations of materials and/or chemical ingredients needed to produce simultaneous presumptive color assays for detection of GHB and/or ROHYPNOL in accordance with the present invention. Accordingly, with the aforementioned in mind, it is apparent that the beverage analysis sampler device, as described herein, has intrinsic abilities and applications associated with the use of additional chemical complexes. Throughout the following chemical detail, it is not the intent to limit the present invention to this example given. The examples set forth hereafter are provided for the purpose of facilitating a full understanding of the nature of the invention in what is considered to be a best mode at this time.

EXAMPLE 1

The following GHB indicator ingredients are combined, as now described:

The crystalline indicator 5,5' Dibromo-o-cresolsulfonphthalein is dissolved in Ethanol, 80% v/v to a level of (5%) five percent by weight. It is then stirred until uniform. Thereafter, 0.007" qualitative filter paper commercially available as WHATMAN # 5, or SCHLEICHER & SCHUELL 8-S filter paper, is immersed in the resulting mixture for ten seconds. After removing the filter paper from this mixture it is exposed to forced hot air for drying, until a deep crimson color is produced. Alternatively, packed cellulose within hollow core 74 of the ampoule partition 70 is saturated with the aforementioned mixture and dried. Presently additional indicators for GHB are under development.

Figures 15, 16:
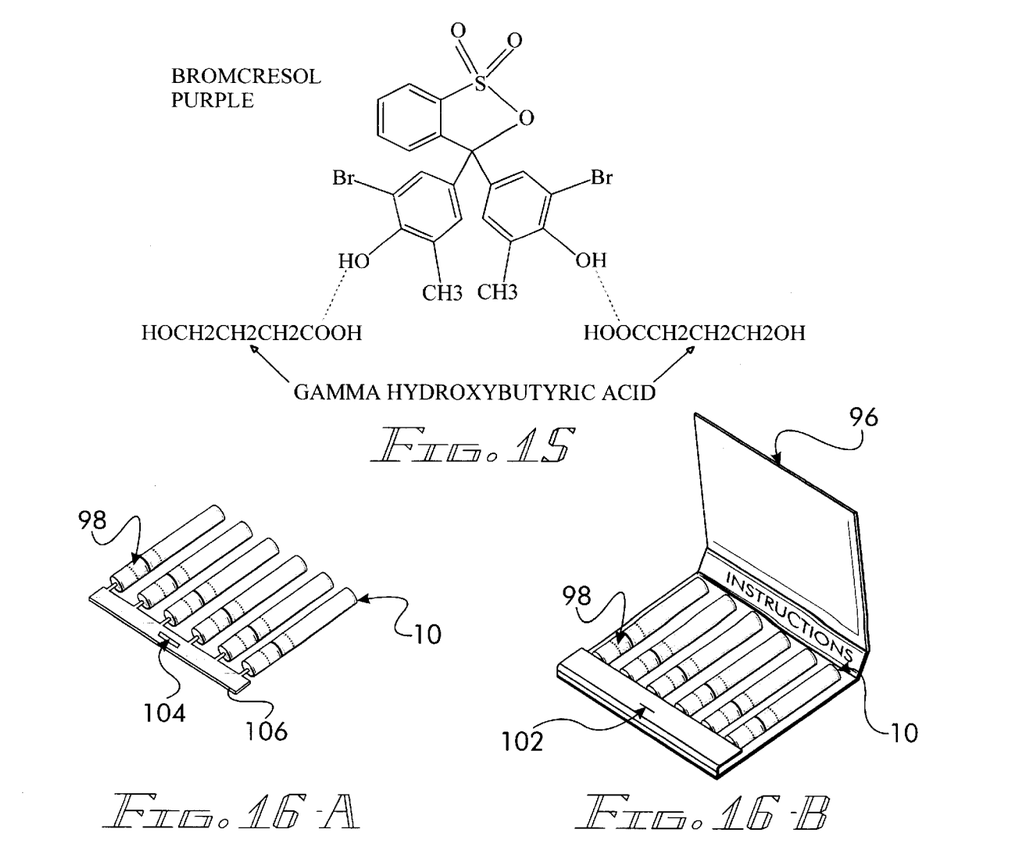
FIG. 15 is a view of the chemical model of GHB and Bromcresol Purple signifying a double bond in accordance with the functional chemistry of the present invention.

Referring to FIG. 15, the unique reaction between BCP or bromcresol purple (5,5' dibromo-o-cresolsulfonphthalein ) and GHB or sodium gamma hydroxybutyrate acid resulting in color species has apparently never been reported in the chemical literature. When combined, BCP and GHB form a strong color complex. The proposed mechanism for color reaction between BCP and GHB is a 1:2 BCP/GHB hydrogen bonded product. Alternatively two water molecules could split out forming direct bonds between BCP and GHB. In either case, the bonding is strong and produces intense color. Condensation products between phenols (such as BCP) and carboxylic acids (such as GHB) can give highly colored (chromophoric) species with conjugated double-bonds.

EXAMPLE 2

The following ROHYPNOL indicator ingredients are combined, as now described:
Zimmermann's Test Reagents for Diazepam The liquid indicators Reagent A (methanolic 2,4-dinitrobenzene) and Reagent B (potassium hydroxide solution) are prepared commercially. The specimen of beverage must come in contact with Reagent A first, preparing the specimen. Then contact with Reagent B will visually qualify the specimen for keto-benzodiazepines. Additional indicators are presently under development and show substantial promise with less concerns for their toxic attributes.

EXAMPLE 3

The following Caffeine indicator ingredients are combined, as now described:

The moist crystal indicator Phosphomolybdic acid is dissolved in Ethanol 80%, v/v to a level of (20%) by weight. This indicator provides a substantial permanent yellow color variant when exposed to concentrated caffeine in an $H_2O$ solution. As can be readily appreciated, the preferred beverage analysis sampler can be provided with an additional embrasure if required. The (3) three embrasures in the caffeine testing version of the beverage analysis sampler device exemplified herein, provide for visual color representation of low, medium, and high levels of caffeine within the beverage being analyzed.

Presently, the premise of this beverage analysis sampler is to have the beverage fluid specimen quantitatively decaffeinated on uptake. This is accomplished by a polymeric adsorbent such as Amberlite resin or activated carbon which retains the caffeine as it is introduced into the ampoule 72. The adsorbents retain specific amounts of caffeine as the fluid migrates by capillary forces, allowing the indicator to verify the level of caffeine. If the specimen is truly decaffeinated no indication will be presented. Presently, there are additional indicators under development for visual color identification of caffeine.

Referring to FIGS. 16A and 16B, the preferred embodiment 10 is shown in a group of (6) six. This multi-pack assembly provides each beverage sampler with a clear, removable plastic sheath 98. This sheath is provided with a perforated or scored zone for ease of removal. The zone travels the circumference of the device and is located at the juncture where the vessel cover 14 meets the support member 12. This sheath resists overall bacterial contamination of the device and retards any unwanted separation of the telescoping assemblies.

Additionally, the multiple units of the beverage analysis sampler device are spaced and contained by a packaging support 106, which is injection molded to the vessels covers of each group of six units. As shown, ease of separation between the packaging support 106 and the beverage sampler 10 is accomplished by a reduction of polymer material where the support meets the vessel cover. Within packaging support 106 resides a rectangular opening or gap 104. This rectangular opening is provided for mounting of the depicted assembly. The assembly is retained within a match book styled cover 96 by means of a metal staple 102 passing through the outer materials of cover 96 and through gap 104.

Referring to the remaining FIGS. 17–25 of the drawings, a reagent test strip 11 in accordance with a second preferred embodiment of the present invention is depicted. In broadest aspect it will be understood that a carrier body is provided which is generally referred to herein as a strip 11, which may be constructed of any suitable shape or form. Strip 11 includes a handle member or support segment 13, which is made to be grasped as a handle by the user of the test strip. Strip 11 also includes an identification segment 15, for the purpose of informing the individual user of this device, the proposed substance to be detected by that particular strip. Strip 11 conveniently further includes an optical display within the analytical reagent indicator segment 17. The optical display is designed in such a way that the presence of the specifically reacting substance is indicated.

In the preferred embodiment, the strip 11 is structured of layered polymer film affording a certain degree of rigidity, yet providing inherent flexibility. This construction provides the device with certain characteristics intrinsic to a complete compactness which is needed to package this device in the desired manner.

The strip 11 shall be structured to accept the varying degrees of temperature ranges associated with common beverages ingested by humans. A flexible polymer strip form is indicated for beverages in temperate liquids, and a plastic stick form is also illustrated for beverages of higher temperatures. However, as will become understood, the device does not need to be immersed (see FIG. 19) into a tumbler 120 of beverage 120 to be effective. Subsequently a droplet or quantity of a beverage to be tested can be applied by varied other means such as, but not limited to, the dipping of an individuals finger into the beverage and placing sufficient droplets in communication with the aperture 29 of strip 11 to complete the test.

The dimensions of the structure are by way of example only. The structure should not be, in any way, restricted to the dimensions conveyed here. For the specific dimensions may be attributed to the analytical variations arising while formatting a specific strip to identify a unique substance. Conveniently the flexible strip is 2.625 inches in length and 0.4 inches in width, plus or minus 0.005.

Typically, the support ranges in thickness from about 0.2 to about 0.08 inches; however, as will be understood, the thickness may, if suitable, vary from this range. The support can be made of thermoplastic materials that after curing do not give off toxic resides and that can be produced and packaged in a sterile environment. Materials for the preferred design criteria and production of this device are readily available. For example, the support medium may be constructed from a combination of two suitable thin, flat films of synthetic material conventionally employed for such purposes. The films are not porous and, after permanently being joined, will provide a liquid impermeable support and chamber 41 within.

Suitable materials for the film are, for example, polyethylene, polypropylene, polyvinyl type polymers, or copolymers, such as polyvinyl chloride, polyvinyl acetate and the like. It is preferable that the support be of the material Ultra - High Molecular Weight Polyethylene which is Food and Drug Administration approved for food contact applications. It has a working temperature range of −26° Degrees Fahrenheit to +180° Degrees Fahrenheit, and a intermittent temperature range of −300° Degrees to +200° Degrees Fahrenheit.

Advantageously, Ultra - High Molecular Weight or High Density Polyethylene provide good chemical and environmental resistance, are non-toxic and have natural white color but, as can be readily appreciated, the material and color may be changed.

Figures 17, 18, 19, 20, 21, 22:
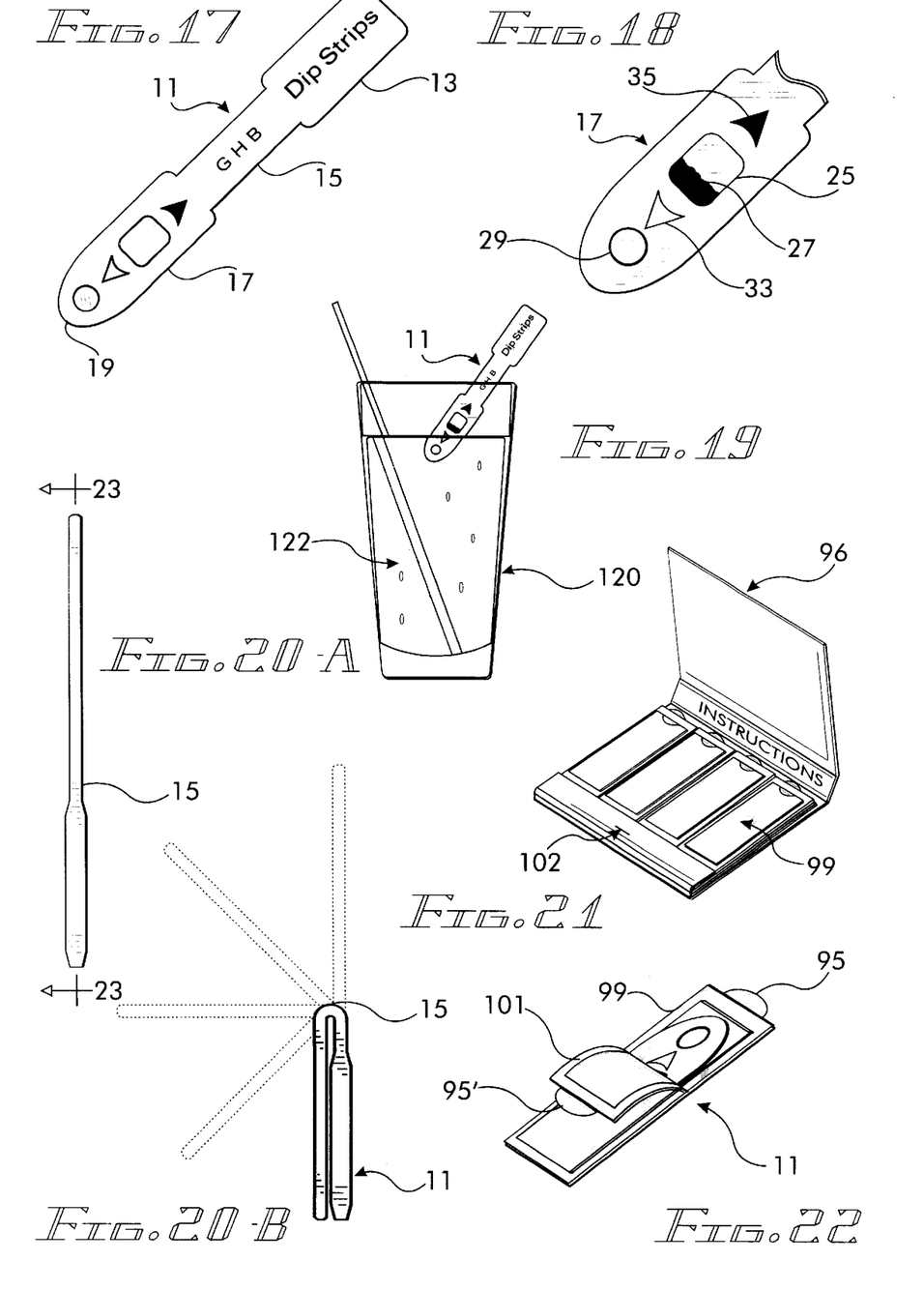
FIG. 17 is a perspective view of a beverage analysis test strip in accordance a second preferred embodiment of the present invention.
FIG. 18 is an exploded view of the beverage analysis test strip of FIG. 17, shown conveying detection by the means of a optical window in accordance with this embodiment of the invention.
FIG. 19 is a perspective view of a preferred test strip as depicted in FIG. 17, inserted into a beverage.
FIG. 21 is a perspective view of a multiple package of the test strips in accordance with a preferred embodiment of packaging means.
FIG. 22 is a top plan view of a single test strip inserted into a sterile sheath.

Strip 11 as indicated in FIG. 17, conveniently includes an identification segment 15, which is typically supplied with lettering in the appropriate language, indicating the substance or substances a particular strip is constructed to detect. It is generally preferable the lettering be black and permanent, however, it can be readily appreciated that the lettering for instance may be a design or drawing and the colors used may be varied.

Strip 11 conveniently includes a calorimetric indicator for visual conformation of the detectable substance within the analytical reagent indicator segment 17, which is typically the portion of the apparatus immersed into a beverage.

Segment 17 is the diagnostic segment of strip 11 and has a greater overall thickness in relationship to the entire apparatus. Segment 17 has numerous intrinsic variations dedicated by the substance a particular strip was designed to detect. Identification of a specific reacting substance in the beverage is visually achieved by creating communication between the beverage to be tested and the analytical reagent, as indicated in FIG. 18. The capillary forces disseminating from a single or dual aperture 29 expose the fluid sample to the reagent, producing a color change 27 contiguous to the optical view embrasure 25, which is located centered between two visual color reference markings portraying the differences between the colors white 33 and black 35. It is understood that the shape may vary for the reason that such a shape is immaterial to the invention. Further the colors rendered here in the detailed description may be varied and depend upon the reagent chemistry employed.

Segment 17 of the preferred embodiment of test strip 11, as indicated in FIG. 17, is shown to be configured with a radius peripheral end 19 geometrically opposed to the handle member. This curved surface provides some penetration into a crushed or chipped ice field within a beverage. It also helps to indicate to the user of the strip which is, the proper end to be immersed into the beverage.

Referring to FIGS. 20A and 20B, by way of illustration it is shown that strip 11 can be folded in half at segment 15 to provide size reduction for packaging.

Referring to FIGS. 21 and 22, a multi-pack of strip 11 is shown. Each strip 11 is packaged in a sterile sheath 99 that is easily removed from package 96. The grouping of strips are held within the package by a standard metal staple 102. Once a single strip is removed from the main package 96, it can be removed from the sterile sheath 99 by separating the adhesive coated 101 opposing layers of the sheath, at tabs 95 and 95' respectfully.

Referring to FIGS. 23–24A and 24B, strip 11 is shown to also be structured with an aperture 29, of which is shown to have a round shape. The size of an aperture circumference is 0.2 inches plus or minus 0.005 inches. The dimension and quantity are by way of example only and will, therefore, provide an understanding of the calculated high tolerance values needed to assure an accurate and responsive device. This dimension is directly proportional to the speed of the analysis observed.

Typically, a preferred approximate elapsed time for analysis of a beverage would within 30 seconds. However, with additional manipulations of strip 11, this time format may alter.

The dimensions and quantity of aperture 29 is determined by calculating the capillary forces at work. This is done by identifying the absorption capabilities of all proposed materials placed within the support chamber 41. It will be understood that the velocity of liquid sample entering the analytical segment 17 is in direct correlation to an individuals perception of the accuracy and quality of the analysis observed during the test procedure. While the shape is immaterial to the present invention, it will become evident that the aperture may have a variety of shapes such as square, round, rectangular, oval, star, triangular, diamond or oblong.

As shown in FIGS. 23–24A and 24B, segment 17 further includes a back-flow prevention membranous structure 37, bound within chamber 41. Accordingly, a membranous structure 35, which is constructed to have one way directional flow for fluids, is sealed along it's peripheral edge to the interior wall of chamber 41. Typically, a test liquid, drawn into chamber 41 by capillary forces into strip 11 through aperture 29, encounters this membranous structure which is aligned with internal capillary forces. It will constrain and inhibit the test liquid from migrating back toward the aperture 29.

Attachment of the membranous structure sufficiently within chamber 41 may be accomplished in a variety of ways. The use of soluble adhesives is not recommended for this purpose. The preferred methods would be that of a molecular weld, such as, but not limited to, sonic welding or a thermo-bonding application. Failure of this seal could result in a quantity of beverage and reagent matrix being released from aperture 29.

Although this would presumably occur only after the analysis has taken place, it is not a preferred option. In the event a strip were to be inadvertently dropped into a beverage, and left, the membranous structure 37 would contain the fluid matrix in chamber 41 and alleviate any relevant concerns about toxicity.

With continued reference to FIGS. 23–24A and 24B, a wick member generally indicated at 57 is encapsulated in segment 17 of strip 11. Advantageously, a water-permeable wick member 57 is provided, sealed within the support chamber 41 and located so as to be exposed by the apertures. The wick member will typically have a thickness of about 0.1 to 0.200 of an inch, with a thickness of about 0.008 of an inch. Materials useful as a wick member are well know to the art, and include polyester, rayon and nitrocellulose filtration substrates. A qualitative filtration material commercially available as WHATMAN # 4 filter paper, is particularly useful.

Other useful materials include woven or matted glass fiber, non-woven and woven fabrics, and other filter papers such as SCHLEICHER & SCHUELL # 604. It will be understood that other water-permeable matrices may be useful.

With continued reference to FIGS. 23–24A and 24B, it may be readily appreciated, in accordance with the present invention, that the wick member 57 be impregnated with or otherwise carry an analyte-modifying agent for chemical modification of the analyte prior to the color-forming reaction. Depending on the matrix of a beverage and with particular reference to the pH and alkalinity of the water and ice, as unknown variables, it may be necessary to add an analyte-modifying agent to the wick member. Typically, acetic acid is beneficial in controlling the pH and alkalinity where adjustments may be needed.

One or more agents may be deposited on or impregnated into wick member 57 to assist in the analysis. If suitable, an additional carrier laden with modifying agents may be used if desired or if deemed appropriate.

Figure 23:
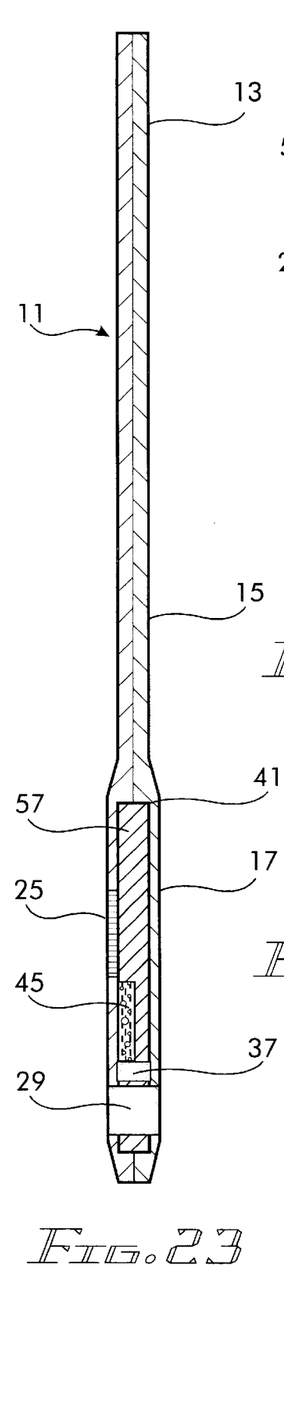
FIG. 23 is a side sectional elevation taken along the plane indicated by the line 23—23 in FIG. 20A, depicting the internal structure of the test strip.
Figure 24:
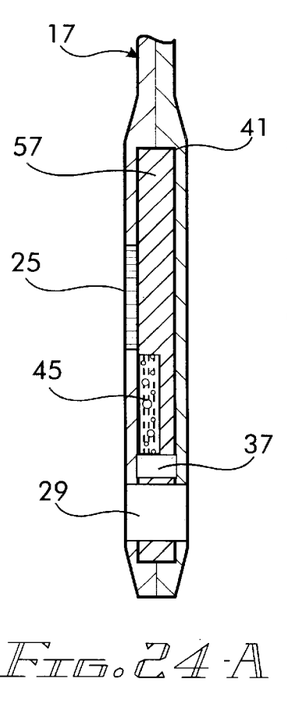
FIGS. 24A–24B are isolated sectional views of a reagent test zone in respective single and multiple staging embodiments of the test strip.

Referring again to FIGS. 23–24A and 24B, a reagent carrier, generally indicated at 45, has one or more reagent indicators deposited on or affixed within or otherwise bound to a typical absorptive carrier of any suitable material known to the art. For example, filtration paper will rapidly absorb the liquid being analyzed. Reagent carrier 45 is shown, as indicated in FIGS. 23 and 24A, placed prior to the embrasure 25. This indicator may be organic or inorganic, but in any event will be suitable for analyzing the beverage. The indicator suitably present on reagent carrier 45 is in an amount sufficient to ensure detection by achieving a strong color complex.

The indicator useful for a presumptive color assay for the detection of Sodium Gamma Hydroxybutyric Acid ($C_4H_7O_3Na$) in a beverage is: 5,5' Dibromo-o-cresolsulfonphthalein. The reagent solution matrix for GHB color indication is the same as previously described.

The indicator useful for a presumptive color assay for the detection of the pharmaceutical Flunitrazepam ($C_{16}H_{12}FN_3O_3$) in a beverage are: Zimmerman's Test Reagent (methanolic 2,4-dinitrobenzene) and (potassium hydroxide). The reagent solution matrix for Flunitrazepam color Indication is as previously described.

The indicator useful for a presumptive color assay for the detection and quantitative analysis of the water soluble alkaloid 1,3,7, Trimethylxanthine ($C_8H_{10}N_4O_2$) in a beverage is: Phosphomolybdic Acid. The reagent solution matrix for 1,3,7, Trimethylxanthine color indication is as previously described.

In addition there are several methods provided to deposit on or embed a carrier with reagent. Typically, the carrier membrane is passed through an impregnation bath containing the particular chemicals so that the carrier becomes saturated with impregnation solution. The carrier membrane is then removed and dried with increased heat. Alternatively, the membrane could be left to dry at room temperature.

Typically, the concentration of reagent or reagent complexes in a impregnation solution and the residence time of the carrier membrane in the solution are selected to ensure deposition of an appropriate amount of the reagent. The residence time allotted will vary from about five to twenty seconds, depending upon the reagent or reagent complexes and the carrier member. If the carrier membrane does not acquire sufficient reagent when initially impregnated an additional deposition may be required to increase the concentration. In any case, the amount of reagent will be sufficient for analysis by visual means.

With continued reference to FIGS. 23–24A and 24B, to increase the capillary forces and fluid capacity additional wick length is afforded. This helps to draw fluid sample past the embrasure 25 allowing for rapid visual conformation.

Referring to FIG. 24B, the multiple embrasures of the proposed quantitative caffeine strip provide a visual means of portraying low 63, medium 65, and high 67 levels of caffeine within the specimen. The colorimetric indicators placed juxtaposed to said windows correlate low 85, medium 87, and high 89 levels of caffeine within the analyzed specimen.

Figure 25:
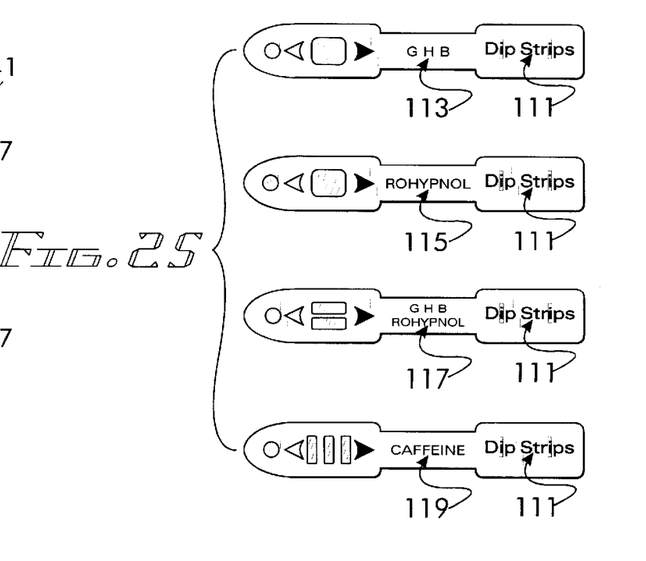
FIG. 25 illustrates labeling criteria associated with the preferred test strip embodiment.

Referring to FIG. 25, the standard overall appearance of a strip may belie the specific usage of a single strip. Visual communication is again used to inform the end user of the proposed function of a specific strip. A label 111 is placed on the support to provide product identification. The specific chemical analysis function of each strip is identified by additional varied labels placed on the support such as, but not limited to, (GHB) 113, (ROHYPNOL) 115, (GHB/ROHYPNOL) 117, (CAFFEINE) 119. As is readily apparent this overall labeling mechanism for product function and representation would be applicable (even with text changes) when placed on the aforementioned, beverage analysis sampler.

While the instant invention has been described in what is considered to be a preferred and practical embodiment, it is recognized that departures may be made within the spirit and scope of the invention which is not to be limited except as set forth in the following claims and within the doctrine of equivalents.

Now that the invention has been described,

What is claimed is:

1. A beverage analysis device comprising:

a housing including an analysis chamber containing at least one chemical reagent composition;

said housing further including means for capturing a fluid specimen taken from a beverage;

at least one aperture in said housing for permitting entry of said fluid specimen from said beverage into said capturing means;

means for isolating said at least one chemical reagent composition from said capturing means and said at least one aperture when capturing the fluid specimen, thereby preventing release of said at least one chemical reagent composition into the beverage;

means for transferring said captured fluid specimen to said analysis chamber wherein said at least one chemical reagent composition, when exposed to said fluid specimen, performs a visible presumptive color assay to identify whether one or more select substances are present in said fluid specimen;

means for protectively containing said transferred fluid specimen and said at least one chemical reagent composition within said housing to prevent release of said transferred fluid specimen and said at least one chemical reagent composition out from said at least one aperture and to prevent contact of said transferred fluid and said at least one chemical reagent composition with said beverage in which the device is inserted;

window means on said housing for viewing said visible presumptive color assay being performed within said analysis chamber.

2. The beverage analysis device as recited in claim 1 wherein said housing includes a main body including said analysis chamber therein and said main body further including a vessel portion for receiving said fluid specimen therein.

3. The beverage analysis device as recited in claim 2 wherein said at least one aperture is disposed in fluid flow communication with said vessel portion for permitting entry of said fluid specimen into said vessel portion.

4. The beverage analysis device as recited in claim 3 wherein said means for containing includes cover means for covering said at least one aperture, said cover means being operable from an initial first closed position, wherein said cover means is covering said at least one aperture, to an open position, wherein said at least one aperture is uncovered to permit fluid flow of said fluid specimen therethrough and into said vessel portion, said cover means being further operable to a second closed position for covering said at least one aperture, thereby capturing said fluid specimen within said main body.

5. The beverage analysis device as recited in claim 4 further including an ampoule containing said at least one chemical reagent composition therein, said ampoule being positioned within said analysis chamber of said main body.

6. The beverage analysis device as recited in claim 5 wherein said ampoule includes an outer seal membrane defining a barrier between said at least one chemical reagent composition and said vessel portion of said main body.

7. The beverage analysis device as recited in claim 6 wherein said means for transferring said captured fluid specimen includes means for puncturing said outer seal membrane upon movement of said cover means to said second closed position, thereby allowing passage of said fluid specimen from said vessel portion into said ampoule for exposure to said at least one chemical reagent composition therein.

8. The beverage analysis device as recited in claim 7 wherein said means for containing includes lock means for locking said cover means relative to said main body upon said cover means reaching said second closed position, thereby containing said at least one chemical reagent composition and said captured fluid specimen within said main body of the device.

9. The beverage analysis device as recited in claim 8 wherein said ampoule contains a plurality of chemical reagent compositions therein.

10. The beverage analysis device as recited in claim 9 wherein said ampoule includes one or more internal permeable membranes separating each of said plurality of chemical reagent compositions therein, wherein said one or more inner permeable membranes are structured and disposed to permit passage of said fluid specimen therethrough.

11. The beverage analysis device as recited in claim 1 wherein said analysis chamber contains a plurality of chemical reagent compositions for performing independent visible presumptive color assays when exposed to said fluid specimen.

12. A beverage analysis device comprising:

a housing having a main body including an analysis chamber containing at least one chemical reagent composition, said main body further including a vessel portion for receiving a fluid specimen;

means for capturing a fluid specimen taken from a beverage within said vessel portion;

at least one aperture in said housing for permitting entry of said fluid specimen from said beverage into said capturing means;

means for isolating said at least one chemical reagent from said capturing means and said at least one aperture when capturing the fluid specimen, thereby preventing release of said at least one chemical reagent composition into the beverage:

means for transferring said captured fluid specimen from said vessel portion to said analysis chamber wherein said at least one chemical reagent composition, when exposed to said fluid specimen, performs a visible presumptive color assay to identify whether one or more select substances are present in said fluid specimen;

means for protectively containing said at least one chemical reagent composition and said transferred fluid specimen within said main body to prevent contact of the at least one chemical reagent composition and the transferred fluid specimen with the beverage in which the device is inserted; and means for viewing said visible presumptive color assay from an exterior of said device.

13. The beverage analysis device as recited in claim 12 wherein said at least one aperture is structured and disposed for permitting entry of said fluid specimen into said vessel portion.

14. The beverage analysis device as recited in claim 12 wherein said analysis chamber contains a plurality of chemical reagent compositions, each of said plurality of chemical reagent compositions being structured and disposed for performing independent visible presumptive color assays when exposed to said fluid specimen to thereby identify whether one or more select substances are present in said fluid specimen.

15. The beverage analysis device as recited in claim 12 wherein said main body is structured and configured in the form of a strip.

16. The beverage analysis device as recited in claim 15 wherein said strip includes one or more sheets of a substrate disposed in overlying relation and sealed about an outer periphery thereof.

17. The beverage analysis device as recited in claim 12 wherein said housing includes at least one portion defining said main body and having a generally tubular structure.

18. The beverage analysis device as recited in claim 12 wherein said housing includes a plurality of portions, including said main body, each of said portions having a generally tubular structure and being telescopically extendible to adjust an overall length of said housing.

19. A beverage analysis device comprising:

a housing having a main body including an analysis chamber containing at least one chemical reagent composition and a vessel portion, said main body further including at least one aperture disposed in fluid flow communication with said vessel portion for permitting entry of a fluid specimen into said vessel portion;

means for capturing said fluid specimen taken from the beverage and including cover means for covering said at least one aperture, said cover means being operable from an initial first closed position, wherein said cover means is covering said at least one aperture, to an open position, wherein said at least one aperture is uncovered to permit fluid flow of said fluid specimen therethrough and into said vessel portion, said cover means being further operable to a second closed position for covering said at least one aperture, thereby capturing said fluid specimen within said main body and isolating said fluid specimen and said at least one chemical reagent composition from the beverage in which the device is inserted;

means for isolating said at least one chemical reagent composition from said capturing means and said at least one aperture when capturing the fluid specimen, thereby preventing release of said at least one chemical reagent composition into the beverage;

means for transferring said captured fluid specimen from said vessel portion to said analysis chamber wherein said at least one chemical reagent composition, when exposed to said fluid specimen, performs a visible presumptive color assay to identify whether one or more select substances are present in said fluid specimen; and means for viewing said visible presumptive color assay from an exterior of said device.

* * * * *